(12) United States Patent
Li et al.

(10) Patent No.: US 6,490,472 B1
(45) Date of Patent: Dec. 3, 2002

(54) MRI SYSTEM AND METHOD FOR PRODUCING AN INDEX INDICATIVE OF ALZHEIMER'S DISEASE

(75) Inventors: Shi-Jiang Li, Brookfield; Piero Antuono, Wauwatosa; Zhu Li; Bharat Biswal, both of Milwaukee; James S. Hyde, Dousman; John L. Ulmer, Brookfield, all of WI (US); Zerrin F. Yetkin, Dallas, TX (US)

(73) Assignee: The MCW Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 09/536,245

(22) Filed: Mar. 27, 2000

Related U.S. Application Data

(60) Provisional application No. 60/152,529, filed on Sep. 3, 1999.

(51) Int. Cl.[7] ............................................... A61B 5/055
(52) U.S. Cl. ...................................... 600/410; 128/920
(58) Field of Search ................................. 600/407, 410, 600/544, 422; 324/309, 307; 382/128; 129/920, 922

(56) References Cited

U.S. PATENT DOCUMENTS

| | | | |
|---|---|---|---|
| 4,952,877 A | 8/1990 | Stormont et al. | ........... 324/312 |
| 4,992,736 A | 2/1991 | Stormont et al. | ........... 324/309 |
| 5,230,346 A | * 7/1993 | Leuchter et al. | ............ 128/731 |
| 5,372,137 A | 12/1994 | Wong et al. | ............. 128/653.5 |
| 5,603,322 A | 2/1997 | Jesmanowicz et al. | ... 128/653.2 |
| 6,104,943 A | * 8/2000 | Frederick et al. | ........... 600/410 |

OTHER PUBLICATIONS

Structural Neuroimaging: Early Diagnosis and Staging of Alzheimer's Disease, Alzheimer's Disease and Related Disorders, De Leon, et al.,pp. 105–125, 1999.
Structural MRI Correlates of Recognition Memory in Alzheimer's Disease, Journal of the International Neuropsychological Society (1998), 4, 106–114, Cahn, et al.
Hippocampal Volumes in Cognitively Normal Persons at Genetic Risk for Alzheimer's Disease, Annals of Neurology, vol. 44, No. 2, Aug. 1998, Reiman, et al.
Volume Loss of the Hippocampus and Temporal Lobe in Healthy Elderly Persons Destined to Develop Dementia, Neurology 48, May 1997, pp. 1297–1304, Kaye, et al.
Brain Atrophy Progression Measured from Registered Serial MRI: Validation and Application to Alzheimer's Disease, JMRI 1997; 7:1069–1075, Fox, et al.
Functional Connectivity in the Motor Cortex of Resting Human Brain Using Echo–Planar MRI, MRM 34:537–541 (1995), Biswal, et al.
24 Functionally Related Correlation in the Noise, Biophysics Research Institute, Medical College of Wisconsin, Hyde, et al. pp. 263–275.

* cited by examiner

*Primary Examiner*—Shawna J Shaw
(74) *Attorney, Agent, or Firm*—Quarles & Brady, LLP

(57) ABSTRACT

Time course MRI data is acquired from the hippocampal region of the brain and processed to produce an index which is a measure of the functional connectivity between locations therein. The MRI data is acquired while the brain is substantially at rest and the spontaneous low frequency component of the time course data at each location in the hippocampus is extracted and compared in a cross-correlation process.

18 Claims, 6 Drawing Sheets

MRI SYSTEM AND METHOD FOR PRODUCING AN INDEX INDICATIVE OF ALZHEIMER'S DISEASE

RELATED APPLICATIONS

This application is based on U.S. Provisional patent application Serial No. 60/152,529 filed on Sep. 3, 1999 and entitled "METHOD FOR DETECTING BRAIN DISEASE USING SPONTANEOUS LOW-FREQUENCY PHYSIOLOGICAL FLUCTUATIONS IN BRAIN ACTIVITY".

This invention was made with United States Government support awarded by NIH; NIH grant numbers DA10214, MH51358 and CA41464. The United Stated Government has certain rights in this application.

BACKGROUND OF THE INVENTION

The field of the invention is the detection of brain disorders using functional magnetic resonance imaging (fMRI) techniques, and particularly the detection of Alzheimer's disease.

Alzheimer's disease is a devastating disease of the brain which results in progressive dementia, physical disability and death over a relatively long period of time. With the aging population in the United States and other countries, the number of Alzheimer's patients is rapidly rising and can accurately be characterized as a silent epidemic. Much research is being conducted to develop drugs that will slow or halt the progression of the disease, and there is hope that a vaccine or inhibitors of secretase may ultimately be developed.

One of the difficulties in managing this disease is the lack of means for its early detection and means for measuring its progression. Such means are needed to identify persons who should receive treatment and to measure the effectiveness of the treatment. An immediate problem is the need for a method which measures the progression of the disease in order to evaluate the effectiveness of the many drugs being developed.

Many techniques have been proposed for detecting and measuring the progress of Alzheimer's disease. These include cognitive tests which attempt to measure brain functions by having the patient perform different tasks. The problem with this approach is that it does not distinguish between dementia caused by Alzheimer's disease and dementia caused by other factors. In addition, the ability to measure the progression of the disease using cognitive tests is very limited.

Neurofibrillary tangles (NFTs) and neuritic plaques (NPs) are the classical neuropathological hallmarks of Alzheimer's disease. Numerous neuropathological studies indicate that the first appearance of NFTs and NPs in the hippocampal region of the brain marks the beginning of the degenerative process. Many studies have been done in which the structure of the brain has been imaged to determine structural changes that are linked to the presence and the progression of Alzheimer's disease. These include: 2-D estimates of size; measures of medial temporal lobe gray matter volume; the qualitative rating of the amount of CSF accumulating in the hippocampal fissures, the size of the suprasellar cistern; and the increased distance between the right and left uncus. None have been particularly successful, and in fact, it has been found that profound structural changes can occur in the brain of some individuals with no cognitive impairment or other symptoms of the disease being evident.

It has been suggested that with progression of Alzheimer's disease, the increased presence of NFTs and NPs in the hippocampus disrupt the perforant pathway and affect functional connectivity. A number of methods have been proposed to assess the functional connectivity in the hippocampal region. The concept of functional connectivity is widely applied to electroencephalogram (EEG) coherence, where it is a measure of the synchronization between two signals across distinct regions of the human brain and is interpreted as an expression of their functional interaction. In positron emission tomography studies, functional connectivity is defined as a spatiotemporal correlation between spatially distinct regions of cerebral cortex. Positron emission tomography (PET) and single photon emission computed tomography (SPECT) can be used to monitor regional cerebral glucose metabolism (rCMRglc) and regional cerebral blood flow (rCBF). It has been found that significant hypoperfusion and hypometablism occur in the region of temporal and parietal association cortices in probable Alzheimer's patients. Many studies have demonstrated the correlation between regional localized hypoperfusion and hypometablism with cognitive deficits seen on behavioral testing. Despite frequent reports of abnormal function in Alzheimer's patients observed by PET and SPECT, however, the clinical utility of these methods is still controversial.

Functional magnetic resonance imaging (fMRI) technology provides a new approach to study neuronal activity. Conventional FMRI detects changes in cerebral blood volume, flow, and oxygenation that locally occur in association with increased neuronal activity induced by functional paradigms. As described in U.S. Pat. No. 5,603,322, an MRI system is used to acquire signals from the brain over a period of time. As the brain performs a task, these signals are modulated synchronously with task performance to reveal which regions of the brain are involved in performing the task. Much research has been done to find tasks which can be performed by patients, and which reveal in an fMRI image acquired at the same time, regions in the brain that function differently when Alzheimer's disease is present. These efforts have to date been unsuccessful.

SUMMARY OF THE INVENTION

The present invention is a method and system for producing an indication of the presence and the progress of a brain disease in a patient by measuring the functional connectivity at different locations therein while the brain is substantially at rest. More particularly, the method includes acquiring a series of NMR image data arrays over a period of time to form a time course NMR image data set, the time course NMR image data set forming a set of time domain voxel vectors in which each time domain voxel vector indicates the NMR signal from a different location in the patient's brain; selecting voxel vectors from locations in the brain affected by the brain disease (e.g. Alzheimer's disease); and producing a connectivity index by cross-correlating the selected time domain voxel vectors. The magnitude of this connectivity index is a good indicator of the presence of Alzheimer's disease and is a quantitative measure of the progress of the disease.

A general object of the invention is to produce a quantitative indication of the presence and progress of Alzheimer's disease in a patient. When the selected region of the brain is the hippocampus, the magnitude of the connectivity index has been found to significantly correlate with the presence of Alzheimer's disease. The lower the connectivity index, the more advanced the disease has progressed.

Another object of the invention is to measure the efficacy of memory enhancing drugs. By providing a quantitative measure of connectivity between selected regions of the brain, the present invention may enable the effect of drugs on memory and other brain functions to be quantitatively measured.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
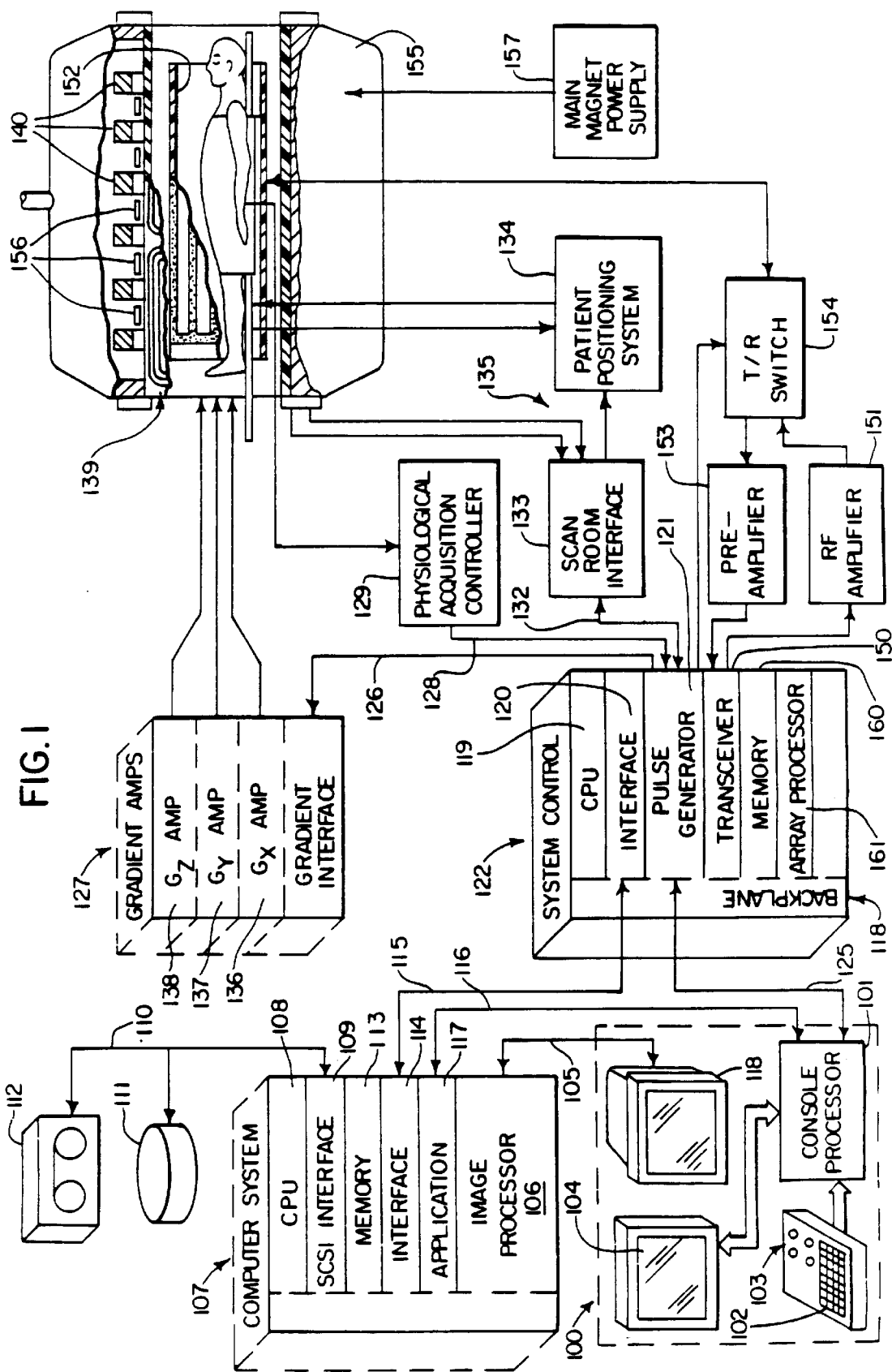
FIG. 1 is a block diagram of an NMR system which employs the present invention.

Referring first to FIG. 1, there is shown the major components of a preferred NMR system which incorporates the present invention and which is sold by the General Electric Company under the trademark "SIGNA". The operation of the system is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 is formed about a backplane bus which conforms with the VME standards, and it includes a number of modules which communicate with each other through this backplane. In addition to the application interface 117 and the image processor 106, these include a CPU module 108 that controls the VME backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan. The pulse generator module 121 also receives patient data through a serial link 128 from a physiological acquisition controller 129. The physiological acquisition control 129 can receive a signal from a number of different sensors connected to the patient. For example, it may receive ECG signals from electrodes or respiratory signals from a bellows and produce pulses for the pulse generator module 121 that synchronizes the scan with the patient's cardiac cycle or respiratory cycle. And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$ and $G_z$ amplifiers 136, 137 and 138, respectively. Each amplifier 136, 137 and 138 is utilized to excite a corresponding gradient coil in an assembly generally designated 139. The gradient coil assembly 139 forms part of a magnet assembly 155 which includes a polarizing magnet 140 that produces a 1.5 Tesla polarizing field that extends horizontally through a bore. The gradient coils 139 encircle the bore, and when energized, they generate magnetic fields In the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed $B_O$, and the total magnetic field in the z direction is referred to as $B_z$, then $G_x = \partial B_z/\partial x$, $G_y = \partial B_z/\partial y$ and $G_z = \partial B_z/\partial z$, and the magnetic field at any point (x,y,z) in the bore of the magnet assembly 141 is given by $B(x,y,z) = B_{O+} G_x x + G_y y G_z z$. The gradient magnetic fields are utilized to encode spatial information into the NMR signals emanating from the patient being scanned. Because the gradient fields are switched at a very high speed when an EPI sequence is used to practice the preferred embodiment of the invention, local gradient coils are employed in place of the whole-body gradient coils 139. As shown in FIG. 11, these local gradient coils are designed for the head and are in close proximity thereto. This enables the inductance of the local gradient coils to be reduced and the gradient switching rates increased as required for the EPI pulse sequence. For a description of these local gradient coils which is incorporated herein by reference, see U.S. Pat. No. 5,372,137 issued on Dec. 13, 1994 and entitled "NMR Local Coil For Brain Imaging".

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate local RF head coil to be used in the transmit and receive mode to improve the signal-to-noise ratio of the received NMR signals. With currently available NMR systems such a local RF coil is necessary in order to detect the small variations in NMR signal produced by brain functions.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

Figure 2:
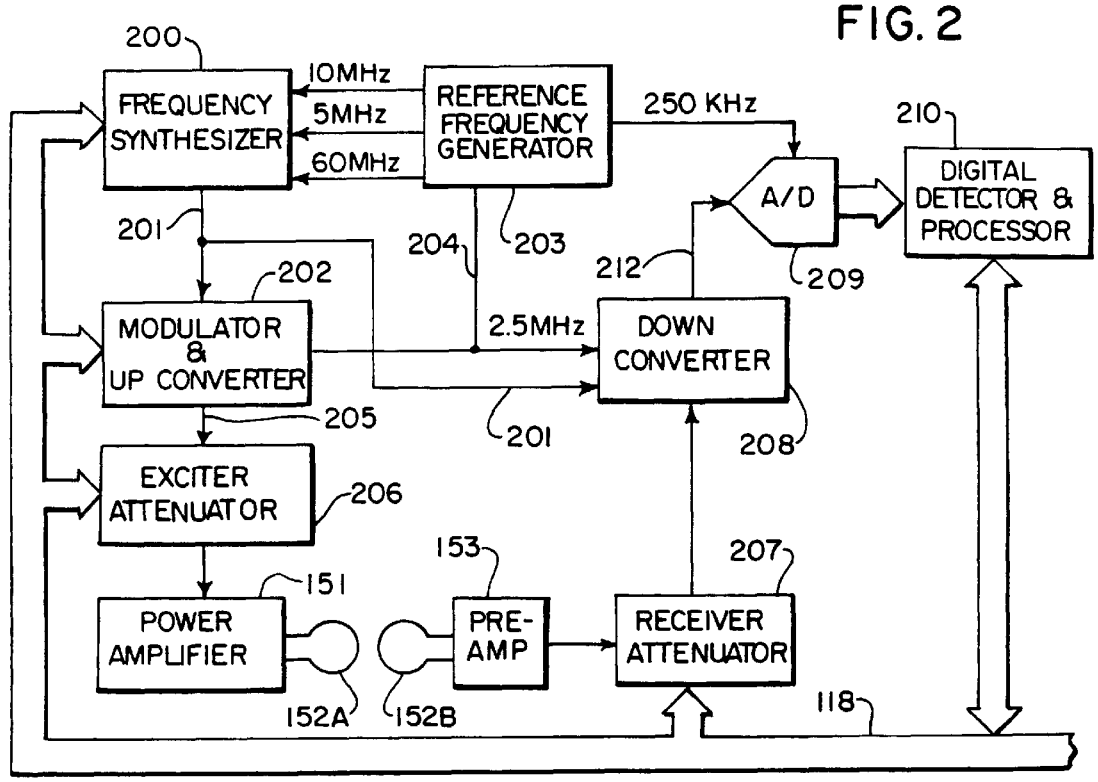
FIG. 2 is an electrical block diagram of the transceiver which forms part of the NMR system of FIG. 1.

The NMR signals picked up by the RF coil are digitized by the transceiver module 150 and transferred to a memory module 160 which is also part of the system control 122. When the scan is completed and an entire array of data has been acquired in the memory modules 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the video display 118 as will be described in more detail hereinafter. Referring particularly to FIGS. 1 and 2, the transceiver 150 includes components which produce the RF excitation field $B_1$ through power amplifier 151 at a coil 152A and components which receive the resulting NMR signal induced in a coil 152B. As indicated above, the coils 152A and B may be a single whole-body coil, but the best results are achieved with a single local RF coil specially designed for the head. The base, or carrier, frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the; desired envelope. These stored digital values may, in turn, be changed from the operator console 100 to enable any desired RF pulse envelope to be produced. The modulator and up converter 202 produces an RF pulse at the desired Larmor frequency at an output 205. The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference. Referring still to FIGS. 1 and 2 the NMR signal produced by the subject is picked up by the receiver coil 152B and applied through the preamplifier 153 to the input of a receiver attenuator 207. The receiver attenuator 207 further amplifies the NMR signal and this is attenuated by an amount determined by a digital attenuation signal (RA) received from the backplane 118. The receive attenuator 207 is also turned on and off by a signal from the pulse generator module 121 such that it is not overloaded during RF excitation. The received NMR signal is at or around the Larmor frequency, which in the preferred embodiment is around 63.86 MHz for 1.5 Tesla. This high frequency signal is down converted in a two step process by a down converter 208 which first mixes the NMR signal with the carrier signal on line 201 and then mixes the resulting difference signal with the 2.5 MHz reference signal on line 204. The resulting down converted NMR signal on line 212 has a maximum bandwidth of 125 kHz and it is centered at a frequency of 187.5 kHz. The down converted NMR signal is applied to the input of an analog-to-digital (A/D) converter 209 which samples and digitizes the analog signal at a rate of 250 kHz. The output of the A/D converter 209 is applied to a digital detector and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained and phase changes in the detected NMR signal accurately indicate phase changes produced by the excited spins. The 2.5 MHz reference signal as well as 5, 10 and 60 MHz reference signals are produced by the reference frequency generator 203 from a common 20 MHz master clock signal. The latter three reference signals are employed by the frequency synthesizer 200 to produce the carrier signal on output 201. For a more detailed description of the receiver, reference is made to U.S. Pat. No. 4,992,736 which is incorporated herein by reference.

As indicated above, local gradient and rf coils are employed to practice the preferred embodiment of the invention. A local coil assembly is comprised of three modular assemblies: a gradient coil assembly; a shield assembly, and an RF coil assembly. The RF coil assembly is comprised of an end capped, bird cage coil which is supported within a molded plastic support structure. The inner opening in the support structure is elliptical in shape to fit snugly around the patients cranium, where as its outer surface is circular in shape and fits snugly within the circular opening in the shield assembly. The shield assembly in turn fits snugly within the circular opening in the gradient coil assembly. For a detailed description of this local coil assembly, reference is made to U.S. Pat. No. 5,372,137 which is incorporated by reference herein.

Figure 3:
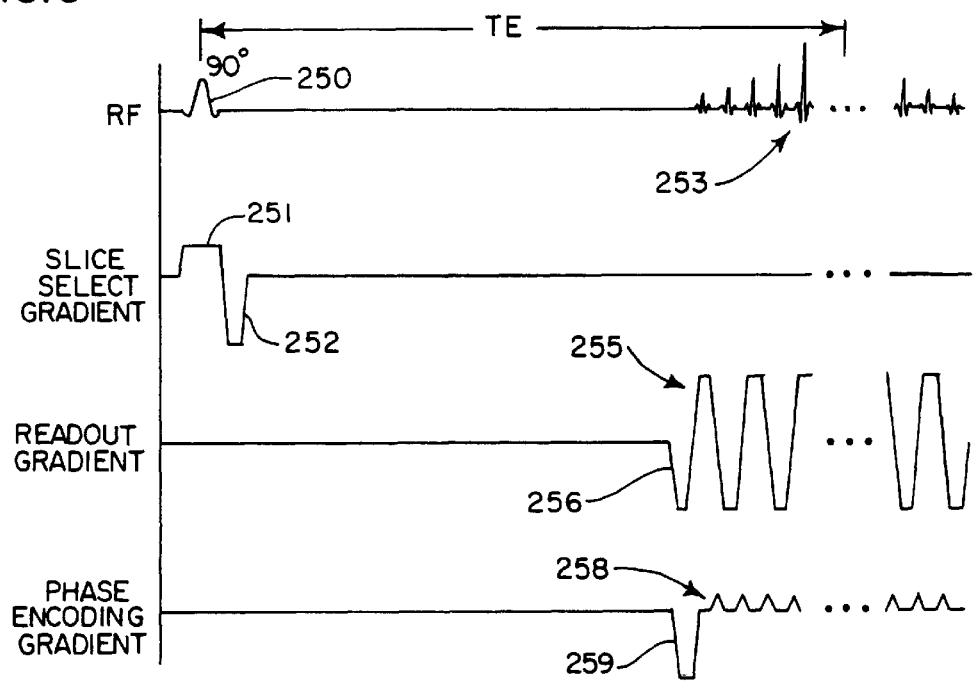
FIG. 3 is a graphic representation of the EPI pulse sequence used to practice the present invention on the NMR system of FIG. 1.

The EPI pulse sequence employed in the preferred embodiment of the invention is illustrated in FIG. 3. A 90° RF excitation pulse 250 is applied in the presence of a $G_z$ slice select gradient pulse 251 to produce transverse magnetization in a slice through the brain ranging from 4 to 25 mm thick. The excited spins are rephased by a negative lobe 252 on the slice select gradient $G_z$ and then a time interval elapses before the readout sequence begins. A total of 64 separate NMR echo signals, indicated generally at 253, are acquired during the EPI pulse sequence. Each NMR echo signal 253 is a different view which is separately phase encoded to scan $k_y$-space from $k_y=-32$ to $k_y=+32$ in monotonic order. The readout sequence is positioned such that the view acquired at $k_y=0$ occurs at the desired echo time (TE). In the preferred embodiment an EPI pulse sequence with TE=40 ms and TR=2 sec. is used. An in-plane resolution of 3.75 mm, a field of view of 24 cm and a slice thickness of 8 mm are used.

The NMR echo signals 253 are gradient recalled echo's produced by the application of an oscillating $G_x$ readout gradient field 255. The readout sequence is started with a negative readout gradient lobe 256 and the echo signals 253 are produced as the readout gradient oscillates between positive and negative values. A total of 64 samples are taken of each NMR echo signal 253 during each 512 microsecond readout gradient pulse 255. The successive 64 NMR echo signals 253 are separately phase encoded by a series of $G_y$ phase encoding gradient pulses 258. The first pulse is a negative lobe 259 that occurs before the echo signals are acquired to encode the first view at $k_y=-32$. Subsequent phase encoding pulses 258 occur as the readout gradient pulses 255 switch polarity, and they step the phase encoding monotonically upward through $k_y$ space.

At the completion of the EPI pulse sequence, therefore, 64 separate frequency encoded samples of 64 separately phase encoded NMR echo signals 253 have been acquired. This 64×64 element array of complex numbers is Fourier transformed along both of its dimensions ($k_y$ and $k_x$) to produce a 64×64 element array of image data that indicates the NMR signal magnitude along each of its two dimensions (y and x).

In order to suppress the signal from cerebral spinal fluid, the EPI pulse sequence may be preceded by an inversion recovery preparation pulse sequence. As is well known in the art, inversion recovery pulse sequences include a 180° rf excitation pulse that inverts the longitudinal spin magnetization, followed by a recovery period TI in which the longitudinal magnetization of the desired spin species recovers, but that of undesired spin species does not. In the preferred embodiment TI is set to 750 milliseconds to suppress the longitudinal magnetization of cerebral spinal fluid spins prior to performing each EPI pulse sequence.

As will be explained in more detail below, the EPI pulse sequence is typically repeated 180 times to acquire time course NMR data for 180 images over a period of 6 minutes.

The acquired NMR data is processed in the conventional manner to produce an NMR image data set for 180 images. As explained above, a two dimensional Fourier transformation is performed by the array processor 161 (FIG. 1) and the resulting NMR image data set is stored in the disk 111 for further processing by the image processor 106 according to the present invention.

Figure 4:
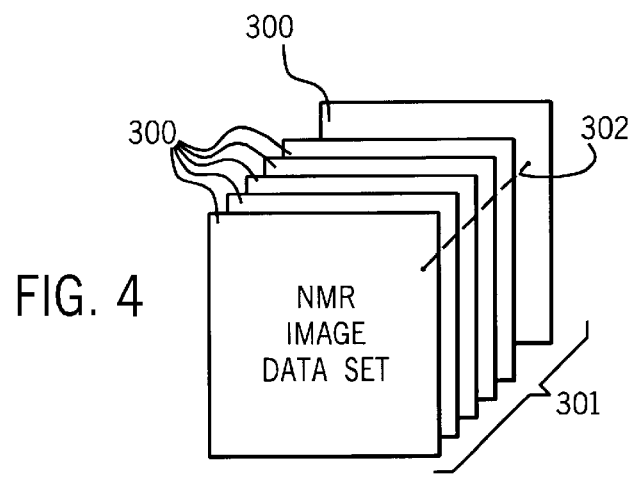
FIG. 4 is a pictorial representation of the NMR image data acquired with the pulse sequence of FIG. 3.

Referring to FIG. 4, this NMR image data set is organized as a set of 64×64 element 2D arrays 300 in which each element stores the magnitude of the NMR signal from one voxel in the scanned slice. Each array 300 can be used to directly produce a 256×256 pixel anatomical image of the brain slice for output to the video display 118. While each array 300 is a "snap shot" of the brain slice at a particular time during the time course study, the NMR image data set may also be viewed as a single 64×64×180 3D array 301 in which the third dimension is time.

The time course NMR image data for one voxel in the array 301 is referred to herein as a time course voxel vector. One such 180 element vector is illustrated in FIG. 4 by the dashed line 302. Each time course voxel vector 302 indicates the magnitude of the NMR signal at a voxel in the image slice over the time course study. A time domain voxel graph 303 of these magnitudes shown in FIG. 5 reveals very clearly variations in the activity of the brain in the region of the voxel.

Figure 7:
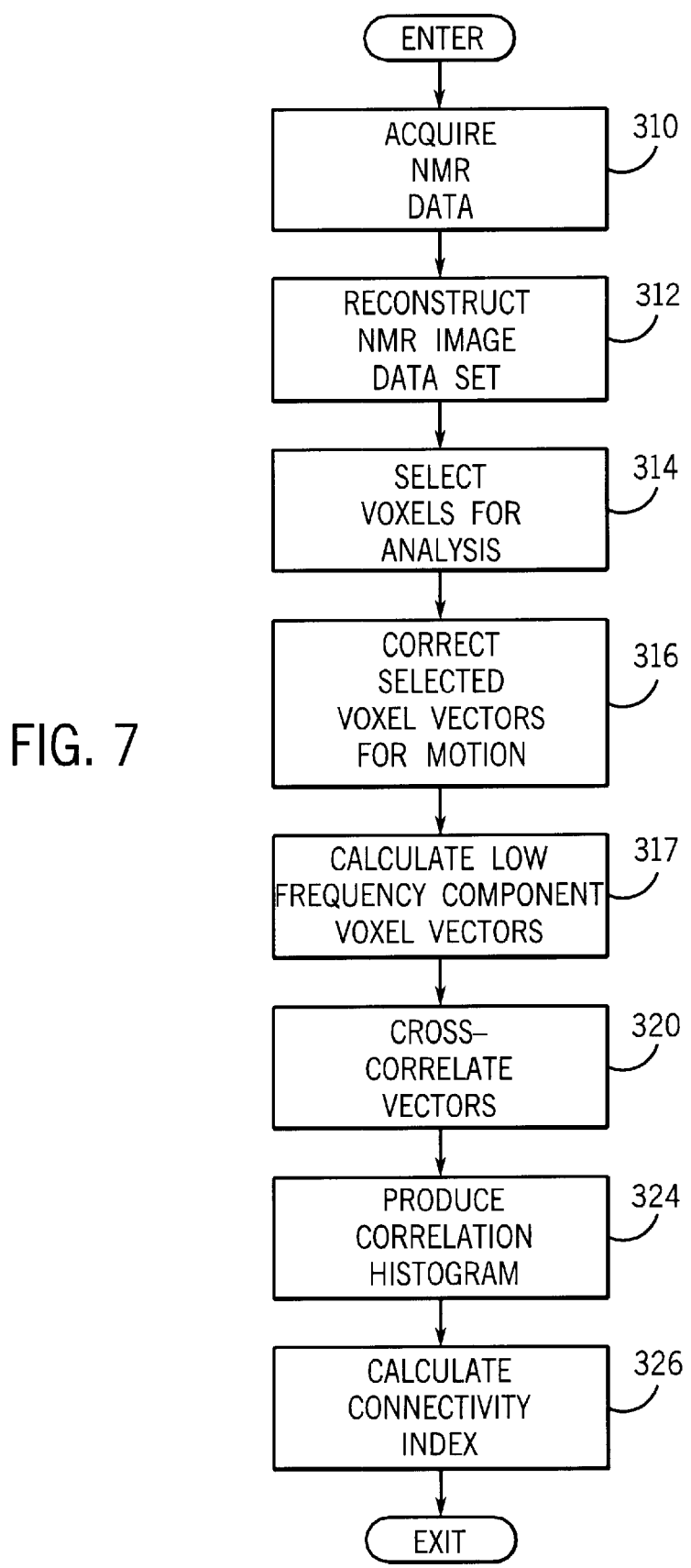
FIG. 7 is a flow chart of the steps required to practice the preferred embodiment of the invention.

Referring particularly to FIG. 7, the first step in producing a connectivity index for Alzheimer's disease is to acquire time course image data from the patient's hippocampus as indicated at process block 310. Foam padding is employed to limit head motion within the local head coil and then localized T1-weighted axial and sagittal plane slices are acquired to provide anatomic images which help define the number of slices and their location for the time course NMR image data acquisition. The above-described EPI pulse sequence is used with TE=40 ms and TR=2 secs and in-plane resolution of 3.75 mm with a field of view of 24 cm and a slice thickness of 8 mm is used. Each session requires about 6 minutes to acquire 15 sagittal slices, with 180 images for each slice. Each of the 15 slices are acquired in an interleaved manner such that the resulting NMR data for each slice is acquired over substantially the same time period. The acquired images are reconstructed as indicated at process block 312 and described above to form the time course NMR image data set 301. In addition, $B_0$ field correction is made by using variable TE at the end of the acquisition series and its phase maps.

Figure 6:
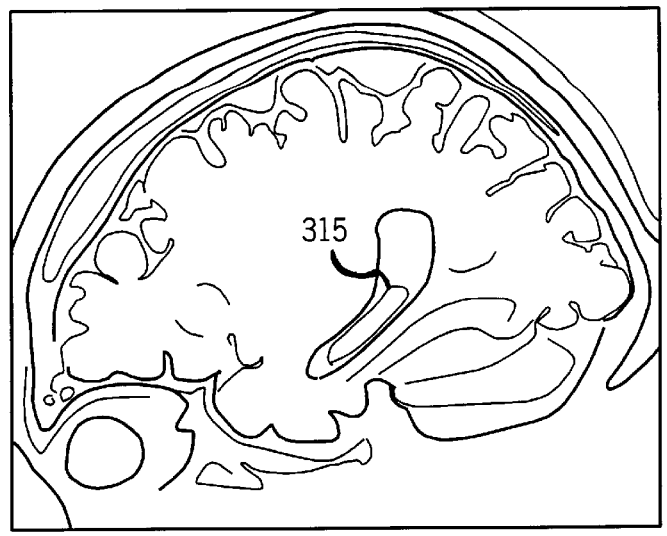
FIG. 6 is a pictorial view of an anatomical image which is produced on a display in the NMR system of FIG. 1.

Using the acquired anatomic images the voxels contained in the hippocampal region of the patient's brain are selected for processing as indicated at process block 314. As shown in FIG. 6 an anatomic image for each acquired slice is displayed and the voxels contained in the hippocampal region indicated at 315 are selected by the operator. A track ball is used to move a cursor over each voxel. This is repeated for each of the 15 sagittal slices such that all the voxels contained in the hippocampus are selected. As a result, voxel vectors 302 are selected from all the acquired slices. These "N" selected voxel vectors 302 are arranged in a linear array 315 illustrated in FIG. 8. It should be apparent to those skilled in the art that hippocampal pixels can also be automatically selected using computer-based hippocampal segmentation.

As indicated at process block 316 the voxel vectors 302 for the selected pixels are corrected for possible patient motion during the scan. In the preferred embodiment this is accomplished using orthognization and the method disclosed by R. W. Cox in *Comput. Biomed. Respectively.* 1996; 39:162–73 entitled *"AFNI: Software for Analysis and Visualization of Functional Magnetic Resonance Neuroimages"*, although other motion correction methods known in the art may also be employed.

Figure 5A:
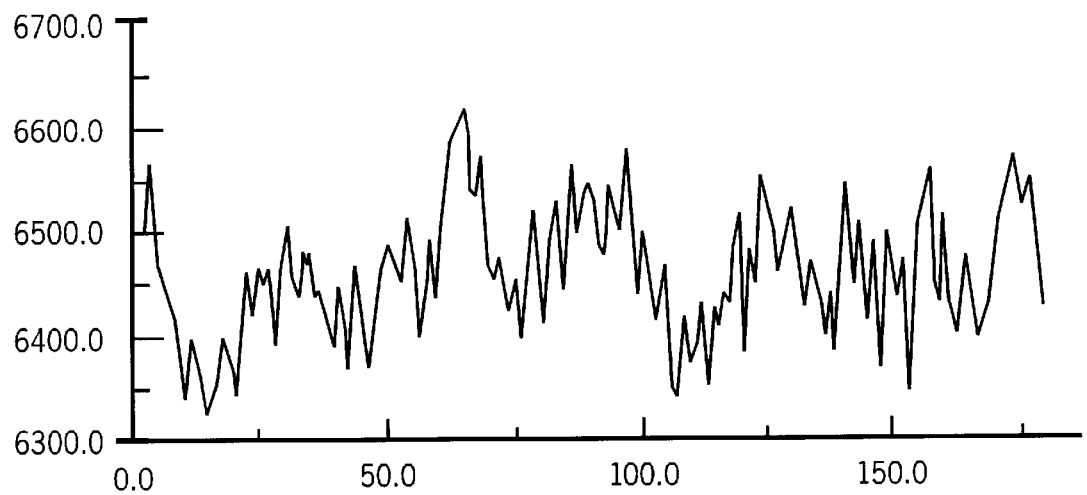
FIG. 5A is a graphic representation of a time domain voxel vector which forms part of the data set of FIG. 4.
Figure 5B:
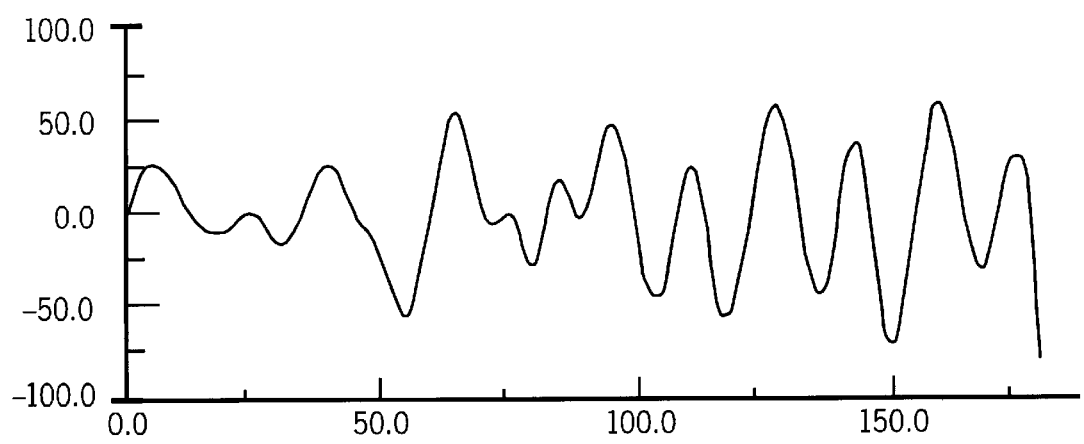
FIG. 5B is a graphic representation of a spontaneous low frequency signal component in the voxel vector of FIG. 5A.

Within each time course voxel vector 302 there are temporal components that correspond to the cardiac and respiratory frequencies, CSF pulsatile motion, and other physiological noise. There is also a low frequency component that corresponds to spontaneous physiological fluctuations. This is illustrated in FIGS. 5A and 5B, where a time course voxel vector signal is shown in FIG. 5A and FIG. 5B illustrates the spontaneous low frequency component which is used for measurement of functional connectivity of the voxels.

As indicated at process block 317, the next step in the process is to produce a set of spontaneous low frequency component voxel vectors 302 in linear array 315. This is accomplished in the preferred embodiment using the singular spectrum analysis method described by J. B. Elsner and A. A. Tsonis, *"Singular Spectrum Analysis: A New Tool in Time Series Analysis"*, published by Plenum Press, NY 1996. Using this method, each voxel vector 302 in the linear array 315 is divided into 166 segments, each segment consisting of 15 consecutive data points. These segments are arranged in a 166×15 matrix, and this matrix is used to obtain its transpose matrix. Using these two matrices, 15 eigen vectors are calculated as a basis function. A total of 15 temporal components are produced and using power spectrum analysis, all but 4 or 5 significant components are eliminated. The second and third temporal components, having a frequency in the 0.01 to 0.08 Hz range are selected as the spontaneous low frequency component of the time course voxel vector. We hypothesize that this component arises from fluctuations in capillary blood flow and oxygenation, which are secondary to neuronal activity.

Figure 8:
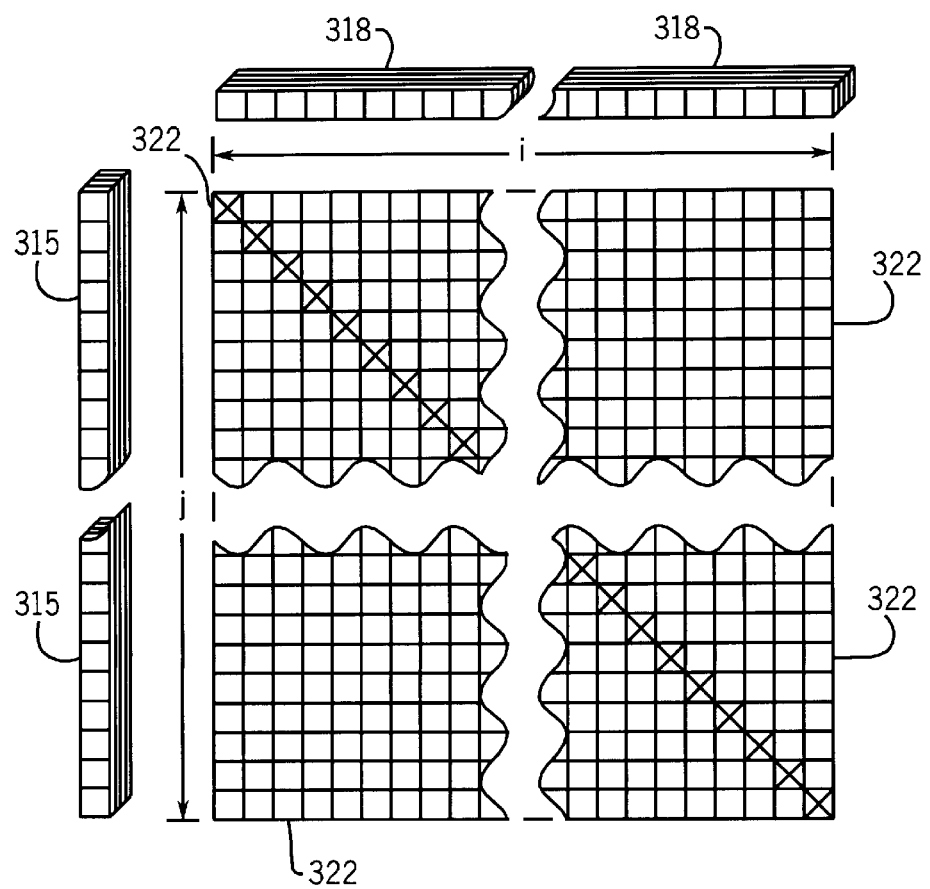
FIG. 8 is a pictorial representation of data structures produced when practicing the preferred embodiment of the invention.

As shown in FIG. 8, the N spontaneous low frequency component voxel vectors are organized in a linear array 318 which corresponds to the linear array 315 of selected voxel vectors from which they are produced. As indicated in FIG. 7 at process block 320, the next step is to calculate the cross-correlation coefficient between each of the N vectors in the array 318 with each of the N vectors in the array 315. In other words, calculate the cross-correlation of the spontaneous low frequency component in each hippocampal voxel with the time course voxel vector of every selected voxel in the hippocampus. In the preferred embodiment the cross-correlation is performed as described in U.S. Pat. No. 5,603,322. With this method the correlation is measured by calculating the dot product of the two vectors. It can be appreciated by those skilled in the art that any method which compares a time course voxel vector with a spontaneous low frequency component voxel vector and produces an indication of the degree of similarity in the two vectors will provide the desired connectivity indication.

A correlation coefficient matrix 322 is produced in which the ij element therein is a result of the cross-correlation of the $i^{th}$ spontaneous low frequency component voxel vector and the $j^{th}$ time course voxel vector. Note that the diagonal values in this matrix are cross-correlating the same voxels, and for this reason these values are eliminated from the following calculations.

As indicated at process block 324, the next step is to produce a correlation histogram which indicates the number of voxels in the hippocampus having the same cross-correlation coefficients. The range of cross-correlation coefficients is divided into "bins" and the number of coefficients in each bin are counted. The final step is to calculate a connectivity index as indicated at process block 326. This is done by calculating the mean value of the histogram. It should be apparent to those skilled in the art that other methods can also be used to produce a connectivity index from the correlation coefficients in the matrix 322.

Figure 9:
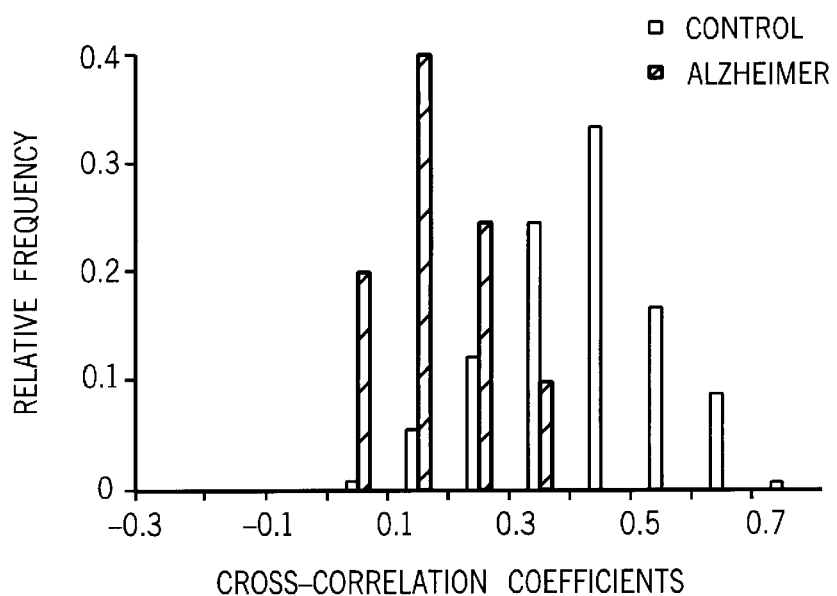
FIG. 9 is a graphic representation of histograms produced in a step of FIG. 7.

Referring particularly to FIG. 9, a histogram of cross-correlation coefficients from the hippocampus of an Alzheimer's patient (dark bars) is compared with the histogram from a normal, control subject (light bars). In this example, the cross-correlation coefficients were obtained from 17 voxels in the right hippocampus, which resulted in 272 cross-correlation coefficients at off-diagonal entries in the correlation coefficient matrix 322. It is readily apparent from these histograms that their mean values are substantially different and that their connectivity indexes are likewise substantially different. A comparison of the two histograms shows no high correlation coefficient on the right side of the curve and less variation for the Alzheimer subject, which suggests lower functional connectivity among pixels in the hippocampal region.

Figure 10:
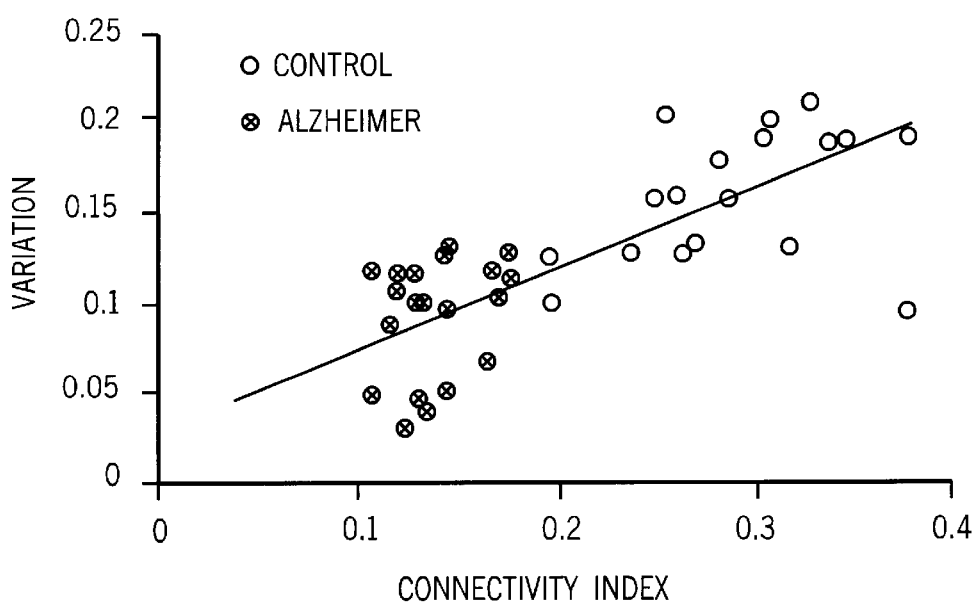
FIG. 10 is a graphic representation of the results when the present invention is employed to measure the connectivity index of a group of Alzheimer's patients and a control group of patients.

We have repeated these measurements in nine control subjects and 10 probable Alzheimer's patients, and the results are shown in FIG. 10 (since each subject has both a left and right hippocampus, the points are doubled). Using the two-tailed Student's t-test, a significant difference in connectivity index values exits between the control group and the probable Alzheimer's disease group (t=11.03, $P<9.79\times10^{-11}$). The index clearly has 100% sensitivity and specificity to separate the control group from the Alzheimer's disease group. Using linear regression analysis, the variation and the connectivity index are significantly correlated (r=0.712, t+6.084, p<0.0001), indicating a lower connectivity index value that corresponds to a lower variation in functional connectivity for the Alzheimer's group.

We have demonstrated that the connectivity index in the hippocampus can be used to distinguish cognitively healthy elderly subjects from Alzheimer's patients with 100% specificity and sensitivity. There are three conceivable mechanisms to support our observation. First, lower connectivity index values measured in the hippocampus in Alzheimer's patients may reflect functional disruption by NFTs and NPs. Second, neuropathological findings suggest that the hippocampus is one of the earliest loci to be affected by NFTs and NPs, and this may explain why the connectivity index has high sensitivity to detect abnormality in the hippocampus. Third, because of the preclinical pathological involvement of the hippocampus in Alzheimer's disease, with disease progression the NFTs and NPs may saturate the hippocampus. This "floor effect" may explain why the connectivity index has high specificity to distinguish Alzheimer's patients from control subjects.

Close inspection of FIG. 10 reveals that the borderline of the connectivity index, which separates the control group and the Alzheimer's group, is around 0.19. We hypothesize that if a subject whose connectivity index in the hippocampus region is around 0.19, the subject may be at high risk to develop Alzheimer's disease. This threshold of 0.19 provides a quantitave evaluation for individuals with different amounts of brain reserve and with different degrees of Alzheimer-type neuropathology. Numerous studies support a threshold model in which Alzheimer dementia is a result of the interplay between brain reserve and Alzheimer-type lesions. When the brain reserve falls below a certain threshold, Alzheimer dementia will occur, and when the brain reserve remains above a certain threshold, Alzheimer dementia will not occur even if many Alzheimer lesions are present. The connectivity index may reflect a person's remaining brain reserve and provide a possible explanation for why a significant number of individuals who meet neuropathological criteria for Alzheimer's disease after death are not cognitively impaired during life.

By applying the concept of threshold and disconnection models of Alzheimer's disease, the measurement of the connectivity index provides an opportunity to objectively study mild cognitive impairment (MCI) subjects. By measuring the connectivity index and its rate of change in MCI patients, we may be able to determine who is destined to develop Alzheimer's disease, who is in the critical phase to develop Alzheimer's disease, and who is undergoing normal aging processes. Also, this method may be very useful to monitor responses and evaluate the efficacy of pharmacological intervention involving symptomatic or preventive drugs. Furthermore, the connectivity index may provide an early marker for Alzheimer's disease in individuals who have no clinical symptoms of Alzheimer's but have a connectivity index below 0.19.

The functional connectivity measured according to the present invention may also be used to detect or measure the progress of other brain disorders. For example, some disorders may be detected by measuring the connectivity between regions in one hemisphere of the brain and regions in the other hemisphere of the brain. In the case of Alzheimer's disease, a connectivity index of 0.19 is a level which indicates its presence. However, in other brain disorders the connectivity level indicating presence of the disease may require separate measurement of other regions of the brain. For example, the connectivity of a region that is not affected by the disease such as the visual cortex part of the brain, may be measured to establish a preset connectivity level which indicates the boundary between normal and diseased connectivity in the region of the brain being examined for disease. In other words, the connectivity level indicating presence of a disease need not necessarily be a fixed connectivity index, but may instead be a connectivity level relative to a non-diseased region of the brain or to a specific region of the brain.

What is claimed is:

1. A method for detecting Alzheimer's disease in the brain, the steps comprising:

measuring the functional connectivity of the brain between a plurality of locations in the hippocampus region of the brain that are affected by the disease, this measurement being made by acquiring image data from the plurality of locations using a magnetic resonance imaging (MRI) system while the brain is substantially at rest; and indicating the presence of the disease when the measured connectivity is below a preset level.

2. The method as recited in claim 1 in which functional connectivity between the plurality of locations in the brain is measured by:

measuring the spontaneous low frequency activity of the brain over a period of time at each location;

comparing the similarity of the measured low frequency activity at said locations; and producing an index which indicates the amount of functional connectivity between the locations.

3. The method as recited in claim 2 in Which the image data is repeatedly acquired over a period of time to produce a time course voxel vector for each of the plurality of locations.

4. The method as recited in claim 3 which includes filtering each time course voxel vector to produce corresponding spontaneous low frequency component voxel vectors, and the comparing operation is performed by cross-correlating spontaneous low frequency component voxel vectors with time course voxel vectors at other locations.

5. The method as recited in claim 4 in which the index is produced by processing the results of the cross-correlation calculations.

6. The method as recited in claim 5 in which the processing of the cross-correlation results includes producing a histogram.

7. The method as recited in claim 5 in which the processing of the cross-correlation results includes calculating the mean value.

8. The method as recited in claim 3 in which the image data is acquired by performing a pulse sequence with the MRI system which includes an inversion recovery preparation sequence having an inversion time that suppresses signals produced by cerebral spinal fluid spins.

9. The method as recited in claim 1 in which the preset level is established by measuring the functional connectivity between a plurality of locations in the brain that are substantially not affected by the disease.

10. The method as recited in claim 9 in which the preset level is established using a plurality of locations in the visual cortex part of the brain.

11. The method as recited in claim 1 in which the functional connectivity is measured by measuring the functional connectivity between a first plurality of locations in one hemisphere of the brain and a second plurality of locations in the other hemisphere of the brain.

12. A system for detecting Alzheimer's disease in a patient, the combination comprising:

a magnetic resonance imaging system for acquiring time course image data from the brain of the patient;

means for selecting a set of time course voxel vectors from the acquired time course image data, each time course voxel vector indicating signal magnitude at a different selected location in the patient's brain over a period of time;

means for producing a set of spontaneous low frequency component voxel vectors, each being produced from a corresponding time course voxel vector by filtering out other frequency components therein;

means for cross-correlating each of the low frequency component voxel vectors with all of the non-corresponding time course voxel vectors and storing the resulting correlation coefficients in a correlation coefficient array;

means for calculating the functional connectivity of the selected locations in the patient's brain using the stored correlation coefficients; and means for indicating the presence of Alzheimer's disease based on the calculated functional connectivity.

13. The system as recited in claim 12 in which the means for selecting includes:

means for producing an image of the patient's brain; and manually operable means for selecting locations in the image which correspond to the hippocampal region of the patient's brain.

14. The system as recited in claim 12 in which the means for calculating includes:
means for producing a histogram of the correlation coefficients which indicates the number of selected locations having correlation coefficients at each of a plurality of correlation coefficient values.

15. The system as recited in claim 14 in which the means for calculating further includes:
means for calculating a connectivity index from the histogram.

16. The system as recited in claim 12 in which the magnetic resonance imaging system includes means for acquiring time course image data from a plurality of slices that intersect the hippocampal region of the patients brain.

17. The system as recited in claim 16 in which the means for acquiring time course image data includes means for performing an echo-planar imaging pulse sequence.

18. The system as recited in claim 16 in which the magnetic resonance imaging system includes a local rf coil disposed around the patient's head and a local gradient coil disposed around the patient's head, both of the local coils being disposed in close proximity to the patient's head.

* * * * *